(12) United States Patent
Mosbaugh et al.

(10) Patent No.: US 8,853,269 B2
(45) Date of Patent: Oct. 7, 2014

(54) COMPOSITION AND METHOD FOR TREATING INFECTIONS AND PROMOTING INTESTINAL HEALTH

(75) Inventors: James David Mosbaugh, Tampa, FL (US); Richard Peter Curtie Calvert, Safety Harbor, FL (US); Eric J. Brooks, Cedar Valley (CA)

(73) Assignee: Copperhead Chemical Company Inc., Tamaqua, PA (US)

( * ) Notice: Subject to any disclaimer, the term of this patent is extended or adjusted under 35 U.S.C. 154(b) by 378 days.

(21) Appl. No.: 13/021,184

(22) Filed: Feb. 4, 2011

(65) Prior Publication Data

US 2011/0200570 A1 Aug. 18, 2011

Related U.S. Application Data

(60) Provisional application No. 61/301,270, filed on Feb. 4, 2010.

(51) Int. Cl.
*A61K 31/225* (2006.01)
*A61K 35/74* (2006.01)

(52) U.S. Cl.
CPC ............. *A61K 31/225* (2013.01); *A61K 35/747* (2013.01); *A61K 35/745* (2013.01); *A61K 35/744* (2013.01)
USPC .................. 514/547; 424/93.45; 424/93.4

(58) Field of Classification Search
CPC . A61K 31/225; A61K 35/747; A61K 35/745; A61K 35/744
USPC ............................ 514/547; 424/93.45, 93.4
See application file for complete search history.

(56) References Cited

U.S. PATENT DOCUMENTS

| | | | |
|---|---|---|---|
| 3,097,098 A | 7/1963 | Allen et al. | |
| 3,158,487 A | 11/1964 | Reid | |
| 5,731,281 A | 3/1998 | Mondin et al. | |
| 2004/0266646 A1 | 12/2004 | Choi | |
| 2005/0112188 A1 | 5/2005 | Eliaz et al. | |
| 2010/0016430 A1* | 1/2010 | Long | ............................. 514/558 |
| 2010/0143533 A1* | 6/2010 | Chang et al. | ...................... 426/2 |

FOREIGN PATENT DOCUMENTS

| | | |
|---|---|---|
| WO | WO 0202716 | 1/2002 |
| WO | WO 0241850 | 5/2002 |
| WO | WO 03106168 | 12/2003 |

OTHER PUBLICATIONS

Notification of Transmittal of the International Search Report and the Written Opinion of the International Searching Authority, or the Declaration, Dec. 15, 2010, PCT Application Serial No. PCT/US10/53053.
Extended European Search Report, Jun. 4, 2013, European Patent Application Serial No. 10824241.3.
Neils, Krog et al., Swelling behaviour of lamellar phases of saturated monoglycerides in aqueous systems, Journal of the Science of Food and Agriculture, Jun. 1, 1973, pp. 691-701.
Rushton, David John, Request for further processing in response to supplementary Search Report of Jun. 4, 2014, filed Apr. 9, 2014, European Patent Application Serial No. 10824241.3.

* cited by examiner

*Primary Examiner* — Brandon Fetterolf
*Assistant Examiner* — Yih-Horng Shiao
(74) *Attorney, Agent, or Firm* — Beck & Thomas, P.C.

(57) ABSTRACT

Compositions and methods for the treatment of intestinal infections. Compositions that include a liquid crystal mixture of an antimicrobial glycerol fatty acid ester and a polyhydric alcohol inhibit the growth of numerous deleterious intestinal pathogenic bacteria, including *C. difficile*. *C. difficile* is the causative agent in an increasing number of antibiotic-resistant bacterial infections. The formulations may be administered orally as capsules or soft gels, or alternatively as a enema, colonic, or rectal suppository. When combined with a probiotic supplement, the liquid crystal combinations reported here are able to treat an intestinal bacterial infection effectively and safely, thus promoting general intestinal health.

24 Claims, 3 Drawing Sheets

Figure 1

| PC-06 | | | Product Concentration in Microtiter Well | | | | | | | | | | POS | NEG |
|---|---|---|---|---|---|---|---|---|---|---|---|---|---|---|
| Microorganism | CFU/ml | MIC | 1 | 2 | 3 | 4 | 5 | 6 | 7 | 8 | 9 | 10 | 11 | 12 |
| C. difficile 43598 | 2.00E+03 | 0.016% | 1.00% | 0.500% | 0.250% | 0.125% | 0.063% | 0.031% | 0.016% | 0.008% | 0.004% | 0.002% | + | - |
| | | | | | | | | | | | | | + | - |

| PC-07 | | | Product Concentration in Microtiter Well | | | | | | | | | | POS | NEG |
|---|---|---|---|---|---|---|---|---|---|---|---|---|---|---|
| Microorganism | CFU/ml | MIC | 1 | 2 | 3 | 4 | 5 | 6 | 7 | 8 | 9 | 10 | 11 | 12 |
| C. difficile 43598 | 2.00E+03 | 0.004% | 1.00% | 0.50% | 0.25% | 0.13% | 0.06% | 0.03% | 0.02% | 0.01% | 0.004% | 0.002% | + | - |
| | | | | | | | | | | | | | + | - |

| PC-07 (repeat) | | | Product Concentration in Microtiter Well | | | | | | | | | | POS | NEG |
|---|---|---|---|---|---|---|---|---|---|---|---|---|---|---|
| Microorganism | CFU/ml | MIC | 1 | 2 | 3 | 4 | 5 | 6 | 7 | 8 | 9 | 10 | 11 | 12 |
| C. difficile 43598 | 6.00E+03 | 0.004% | 1.00% | 0.50% | 0.25% | 0.13% | 0.06% | 0.03% | 0.02% | 0.01% | 0.004% | 0.002% | + | - |
| | | | | | | | | | | | | | + | - |

Figure 2

| BPS-K-360 (9/7/10) | | | Product Concentration in Microtiter Well | | | | | | | | | | No Growth | | POS | NEG |
|---|---|---|---|---|---|---|---|---|---|---|---|---|---|---|---|---|
| | | | | | | | | | | | | | | Growth | | |
| Microorganism | CFU/ml | MIC | 1 | 2 | 3 | 4 | 5 | 6 | 7 | 8 | 9 | 10 | 11 | 12 | | |
| C. difficile 43598 | 5.00E+03 | <0.008% | 4.00% | 2.00% | 1.00% | 0.50% | 0.25% | 0.125% | 0.063% | 0.031% | 0.016% | 0.008% | + | - | | |

Figure 3

| | X-K-18 | | Product Concentration in Microtiter Well | | | | | | | | | | Growth POS | No Growth NEG |
|---|---|---|---|---|---|---|---|---|---|---|---|---|---|---|
| Microorganism | CFU/ml | MIC (%) | 1 | 2 | 3 | 4 | 5 | 6 | 7 | 8 | 9 | 10 | 11 | 12 |
| Bifidobacterium bifidum | 4.50E+04 | 0.0039 | 0.2500 | 0.1250 | 0.0625 | 0.0313 | 0.0156 | 0.0078 | 0.0039 | 0.0020 | 0.0010 | 0.0005 | + | - |
| Lactobacillus acidophilus | 2.75E+05 | 0.0020 | 0.2500 | 0.1250 | 0.0625 | 0.0313 | 0.0156 | 0.0078 | 0.0039 | 0.0020 | 0.0010 | 0.0005 | + | - |
| | | 0.0020 | | | | | | | | | | | + | - |
| Saccharomyces boulardii | 1.05E+06 | 0.0010 | 0.2500 | 0.1250 | 0.0625 | 0.0313 | 0.0156 | 0.0078 | 0.0039 | 0.0020 | 0.0010 | 0.0005 | + | - |
| | | 0.0010 | | | | | | | | | | | + | - |

COMPOSITION AND METHOD FOR TREATING INFECTIONS AND PROMOTING INTESTINAL HEALTH

CROSS-REFERENCE TO RELATED APPLICATION

The present application claims the benefit under 35 U.S.C. §119(e) of U.S. Provisional Application No. 61/301,270 filed Feb. 4, 2010.

FIELD OF THE INVENTION

The present invention relates generally to a method and composition for treating intestinal disorders using natural fatty acid esters and probiotics. More specifically, the present invention relates to a natural, soluble, highly concentrated form of fatty acid ester antimicrobial that is effective in inhibiting the growth of pathogenic intestinal bacteria. In particular, the present invention relates to the administration of a natural fatty acid ester to inhibit the growth of infectious or pathogenic intestinal bacteria such as *Clostridium, Clostridium difficile, Salmonella typhosa, Salmonella paratyphi, Salmonella schottmuelleri, Shigella dysenteriae, Shigella flexneri, Proteus vulgaris, Pseudomonas aeruginosa, Listeria* and *Escherichia coli*. In addition, *Bacteroides* species such as *B. fragilis, B. uniformis*, are inhibited by polyglycerol and monolaurin. The present invention may be used in concert at appropriate intervals with the administration of a probiotic supplement.

BACKGROUND OF THE INVENTION

The healthy intestines of mammals contain billions of colonies of bacteria, bacteria that have evolved with mammals that typically, and under optimal health conditions of the mammal, function in a synergistic manner with the host mammal. Unfortunately, the widespread use of antibiotics, especially broad-spectrum antibiotics, has led to deleterious pathological conditions. The physiological health of the gastrointestinal tract is dependent on the health of its bacterial population, or its "microflora." A plurality of individual bacterial species inhabit the gastrointestinal tract and their growth and metabolism depend primarily upon the substrates available to them, most of which are derived from the diet. The administration of antibiotics does kill harmful pathogens, but antibiotics do not discriminate between harmful pathogens and beneficial, non-pathogenic microorganisms resident in the flora. The beneficial microorganisms, typically the lactic acid producing microorganisms, are destroyed by antibiotics and impair health and digestive function. A result of the proliferation of harmful bacteria species is infection from toxic by-products resulting in diarrhea and damage to mucosal lining. Absorption and assimilation of food and bioactive ingredients are disturbed and at the same time there may be relapse (the return of infections and their accompanying signs and symptoms).

Other deleterious results of indiscriminate use of antibiotics is the generation of multiple antibiotic-resistant pathogens and occurrence of secondary opportunistic infections which often result from the depletion of lactic acid producing and other beneficial flora within the gastrointestinal tract. Methicillin-resistant *Staphylococcus aureus* (MRSA) infections and vancomycin-resistant Enterococci (VRE) have been reported. The development of such resistance has led to numerous reports of systemic infections that are not treatable with conventional antibiotic therapies.

*Clostridium difficile* is a Gram-positive facultative anaerobic bacteria that is widespread in human intestinal flora that, when its growth is unchecked by other bacteria, produces toxins that cause debilitating and life threatening colitis. *Clostridium difficile*, often called *C. difficile* or "*C. diff*," can cause symptoms ranging from diarrhea to life-threatening inflammation of the colon. Illness from *C. difficile* most commonly affects older adults in hospitals or in long term care facilities and typically occurs after use of antibiotic medications. In recent years, *C. difficile* infections have become more frequent, more severe and more difficult to treat. Each year, tens of thousands of people in the United States became ill from *C. difficile*, including some otherwise healthy people who are not hospitalized or taking antibiotics.

*C. difficile* bacteria can be found throughout the environment—in soil, air, water, and human and animal feces. A small number of healthy people naturally carry the bacteria in their large intestine. *C. difficile* is most commonly found in hospitals, nursing homes, extended care facilities, nurseries for newborn infants, institutions and other health care facilities, where a much higher percentage of people carry the bacteria. *C. difficile* may also be present in communal animal environments such as kennels, barns, and stables. When *C. difficile* grows unchecked, it produces two primary toxins, known as Toxin A and Toxin B, that trigger the formation of a psuedomembrane in the colon line that interferes with the normal function of the organ which can be permanent.

*C. difficile* colitis is widespread. The bacteria are passed in feces and spread to food, surfaces and objects when people who are infected do not wash their hands thoroughly. The bacteria produce hardy spores that can persist in a room for weeks or months. An estimated 500,000 cases are treated each year in North America and the problem is reported to be particularly severe in Canada and the UK. Annual death rates have been estimated at 20,000 for the US and 8,000 in the UK. A typical hospital stay for *C. difficile* colitis lasts from seven to ten days, so the costs of hospitalization alone are estimated at more than a billion dollars annually.

People in good health do not usually become ill from *C. difficile*. The intestines contain millions of bacteria, many of which naturally help protect the body from *C. difficile* infection. Antibiotics, taken to treat an infection, can destroy the normal, natural flora in addition to destroying the bacteria causing the illness. When the normal intestinal flora is compromised, *C. difficile* can quickly grow out of control. The antibiotics that most often lead to *C. difficile* infections include fluoroquinolones, cephalosporins, clindamycin and penicillins.

*C. difficile* disease is believed to be caused by the actions of two exotoxins, toxin A and toxin B, on gut epithelium. Both toxins are high molecular weight proteins (280-300 kDa) that catalyze covalent modification of Rho proteins, small GTP-binding proteins involved in actin polymerization, in host cells. Modification of Rho proteins by the toxins inactivates them, leading to depolymerization of actin filaments and cell death. Both toxins are lethal to mice when injected parenterally (Kelly and Lamont, *Annu. Rev. Med.*, 49:375-90, 1998).

Exotoxins A and B which are produced by pathogenic strains of the bacterium are cytotoxic, enterotoxic, proinflammatory, and are considered to be the main virulence factors of this non-invasive microorganism. However, not all infections with toxigenic strains result in disease, prompting the search for additional virulence factors. Bacterial surface-expressed antigens represent candidate virulence factors, and are also considered important since such proteins likely mediate the essential functions such as adhesion to the epithelial layer of the gut in the first step of colonization or interaction with mediators of local immunity. In common with many other bacteria, *C. difficile* expresses a crystalline or paracrystalline surface layer (S-layer) on the outer cell surface. Such S-layers comprise proteins or glycoproteins forming a regularly arranged lattice on the external surface of the bacterium, and have previously been shown to be essential for the virulence of pathogens such as *Aeromanas salmanicida* and *Campylobacter fetus*. In contrast to most bacteria which comprise one S-layer, *C. difficile* is known to comprise two superimposed paracrystalline S-layers, each composed of a glycoprotein subunit which varies slightly in apparent molecular weight among different *C. difficile* strains. Most strains of *C. difficile* express two major S-layer proteins (SLPs), one of 32-38 kDa (low-MW SLP) and a second of 42-48 kDa (high-MW SLP). The low-MW SLP appears to be immunodominant and is the antigen most commonly recognized by patients suffering from *C. difficile* infections, and is the only antigen recognized in EDTA extracts of bacteria by antisera raised in rabbits against whole *C. difficile* cells (Calabi, E. et al., 2001, *Mol. Microbiol.*, 40 (5) p 1187-99, PMID: 11401722).

The typical case of *C. difficile* colitis has one or more of the following characteristics: the patient is elderly and either lives in an institution or has been hospitalized for more than a week; the patient has undergone a course of antibiotics for an unrelated illness, often an upper respiratory infection or to prevent an infection after dental surgery; the patient has had *C. difficile* colitis before (the recurrence rate after successful therapy is roughly 20%).

*C. difficile* illness usually develops during or shortly after a course of antibiotics. Signs and symptoms may not appear for weeks or even months afterward. The most common symptoms of mild to moderate *C. difficile* disease are watery diarrhea three or more times a day for two or more days and mild abdominal cramping and tenderness.

In more severe cases, *C. difficile* causes the colon to become inflamed (colitis) or to form patches of raw tissue that can bleed or produce pus (pseudomembranous colitis). Signs and symptoms of severe infection include: Watery diarrhea 10 to 15 times a day, abdominal cramping and pain, which may be severe; fever; blood or pus in the stool; nausea; dehydration; loss of appetite; and weight loss.

As with many anaerobes, *C. difficile* forms spores that can accumulate on surfaces in institutions and may become airborne. These spores are resistant to many of the disinfectants typically used in hospitals and institutions. An aggressive strain of *C. difficile* has emerged that produces far more deadly toxins than other strains do. The new strain is more resistant to certain medications and has been found in patients who have not been in the hospital or taken antibiotics. This strain of *C. difficile* has caused several outbreaks of illness since 2000. Conventional therapy for *C. difficile* colitis includes administration of antibiotics such as bacitracin, cefprozil, meropenem, metronidazole, nitazoxanide, ticarcillin; clavulanic acid, tinidazole, and vancomycin. These antibiotics have severe side effects and are prescribed only when absolutely needed in order to delay the evolution of vancomycin-resistant strains of *Clostridium* and other bacteria.

If left untreated, *C. difficile* can lead to serious illness. Complications include dehydration, kidney failure, bowel perforation, toxic megacolon, and in some cases death. Severe diarrhea can lead to a significant loss of fluids and electrolytes, making it difficult for the body to function normally and possibly resulting in a drop in blood pressure. In some cases, dehydration can occur so quickly that kidney function deteriorates. *C. difficile* can cause extensive damage to the lining of the large intestine resulting in a perforated bowel. A perforated bowel can spill bacteria from the intestine into the abdominal cavity, leading to life-threatening peritonitis. The colon can become grossly distended when it is unable to expel gas and stool resulting in a toxic megacolon. Even in mild to moderate *C. difficile* infections, the infection can quickly progress to a fatal disease if not treated promptly.

In addition to antibiotic treatments, other therapies are reported to have a positive effect on the disease. For example, probiotics, the introduction of beneficial strains of bacteria through supplements and foods, have been shown to be beneficial in preventing *C. difficile* infections in populations of elderly and healthy people undergoing antibiotic therapies. Probiotics are organisms, such as bacteria and yeast, which help restore a healthy balance to the intestinal tract. A natural yeast called *Saccharomyces boulardii*, in conjunction with antibiotics, has been accepted as effective in helping prevent recurrent *C. difficile* infections. Probiotic therapy, however, does not directly inhibit the proliferation of *C. difficile*; rather, the therapy indirectly addresses the pathogen through competitive inhibition, that is, by promoting the growth of bacteria that compete with it in the confines of the intestines. Furthermore, the clinical literature does not support the use of probiotics alone in the treating *C. difficile* infections. In severe infections, surgery to remove a diseased portion of the colon may be performed.

Approximately 20% of people who have been infected with *C. difficile* get sick again, either because the initial infection never went away or because they become re-infected with a different strain of the bacterium. Treatment for recurrent disease may include: antibiotics, which may involve one or more courses of a medication, a longer course of treatment, or an antibiotic given once every two days; probiotics, such as *S. boulardii, Lactobacillus acidophilus, Bifidobacterium bifidum, Bifidobacterium longum*, and *Bifidobacterium lactis* given along with the antibiotic medication; or stool transplant (fecal bacteriotherapy) to restore healthy intestinal bacteria by placing donor stool in your colon. Although this is rarely done in practice, research has shown stool transplant to be helpful in selected cases.

In some implementations probiotics are microbial-based dietary adjuvants that beneficially affect the host physiology by modulating mucosal and systemic immunity as well as improving nutritional & microbial balance in the intestinal tract. [Naidu, N., Bidlack, W. R., Clemens, R. A. Probiotic Spectrum of Lactic Acid Bacteria (LAB), *CRC Critical Reviews in Food Science and Nutrition*, 39: 113-126, 1999.] In other implementations probiotics are used in a preparation of or a product containing viable, defined microorganisms with or without other substances in sufficient numbers, which improve or alter the micro flora or their properties (by implantation or colonization) in a compartment of the host and by that exert beneficial health effects in this host. Thus, probiotics may be applied to tissue extracts that stimulate microbial growth. It can also be deemed to mean organisms and substances which contribute to intestinal microbial balance or, alternatively, a live microbial feed supplement which beneficially affects the host animal by improving its intestinal microbial balance.

Evidence indicates significant, positive health effects through the use of probiotics including, but not limited to: 1) reduction of *Helicobacter pylori* infection; 2) reduction of allergic symptoms; 3) relief from constipation; 4) relief from irritable bowel syndrome; 5) beneficial effects on mineral metabolism, particularly bone density and stability; 6) cancer prevention; and 7) possible reduction of cholesterol and triacylglycerol plasma concentrations.

Probiotic dietary supplements generally include organisms that are non-pathogenic and non-toxigenic, retain viability during storage, and survive passage through the stomach and the small intestine. Modification of the structure and metabolic activity of microflora is achieved through diet, primarily by administering probiotic live microbial food supplements. Different microorganisms prefer different habitats that may differ from host to host species. The best-known probiotics are the lactic acid-producing bacteria (i.e., Lactobacilli) and Bifidobacteria. Lactobacilli are a helpful type of bacteria naturally occurring in the intestines and constitute a major part of intestinal flora. Since all probiotics do not permanently colonize the host, they need to be ingested regularly for any health-promoting properties to persist. Commercial probiotic preparations generally comprise mixtures of Lactobacilli and Bifidobacteria. Different strains of probiotic bacteria may exert different effects based on specific capabilities and enzymatic activities, even within one species. Bacteria colonizing high-transit-rate sites, such as the small intestines, must adhere firmly to the mucosal epithelium and must adapt to the milieu of this adhesion site. The competition for adhesion receptors between probiotic and pathogenic microorganisms, therefore, is dependent on the habitat specifics.

Most lactic acid-producing or probiotic bacteria are extremely sensitive to common antibiotic compounds. Even during a normal course of individual antibiotic therapy, many individuals develop a number of deleterious physiological side-effects including: diarrhea, intestinal cramping, and sometimes constipation. These side effects are primarily due to the non-selective action of antibiotics as discussed herein. Thus, individuals taking antibiotics often suffer from gastrointestinal problems as a result of the beneficial microorganisms (i.e., intestinal flora), which normally colonize the gastrointestinal tract, being killed or severely attenuated. The resulting change in the composition of the intestinal flora can result in vitamin deficiencies when the vitamin-producing intestinal bacteria are killed, diarrhea and dehydration and, more seriously, illness should a pathogenic organism overgrow and replace the remaining beneficial gastrointestinal bacteria. Further, as a result of rapid evacuation of the bowels during diarrhea, a significant amount of the therapeutic compounds also do not get absorbed and are lost in the feces.

The interest in the use of novel, therapeutic agents other than antibiotics to treat *C. difficile* has grown over the past decades as the prevalence of infection has increased. Certain fatty acid esters have been noted for their potent antimicrobial effects. U.S. Patent Application No. 61/252,269 by Calvert et al., which is hereby fully incorporated by reference, discloses a novel liquid crystal delivery system comprised of antimicrobial compounds. Those compositions allow the use of medium chain glycerol fatty acids and/or their esters with enhanced solubility that provides broad range antimicrobial properties. Those antimicrobial compositions have been found to be extremely effective in inhibiting the growth of *C. difficile*. The most potent medium chain fatty acid has been found to be lauric acid ($C_{12}$) and/or its monoglyceride glycerol monolaurate. The glycerol ester of lauric acid is a natural component of breast milk. Whereas infant nurseries commonly test positive for *C. difficile*, infant very rarely express the symptoms of *C. difficile* infection. A combination of a concentrated, soluble monolaurin with appropriate probiotic regimen administered at alternate intervals is a viable treatment for *C. difficile* infection while having no apparent negative effect on healthy or symbiotic Gram-positive or Gram-negative intestinal bacteria.

Even though glycerol monolaurate has been shown to be an effective broad range antimicrobial agent, low solubility and the formation of microcrystalline structures in situ have limited its use in practical applications. Glycerol monolaurate is typically used in concentrations in commercial formulations between 1-2%. Even at such low concentrations, formulations containing glycerol monolaurate are unstable such that the use of surfactants, emulsifiers, or other stabilizing agents is required.

Attempts to increase the solubility of glycerol monolaurate, and other fatty acids esters, diglycerides, triglycerides, etc. have been the focus of much research and development. It was found by U.S. Patent Application No. 61/252,269 by Calvert et al. that many of the common emulsifying mechanisms, for example the use of surfactants and emulsifiers with various hydrophile/lipophile balance values and combinations thereof, can render the active ingredient ineffective. That is, the act of emulsifying glycerol monolaurate with traditional emulsifiers reduces or eliminates its antimicrobial properties. Thus, the prior art has encountered a long-standing problem when attempting to include such anti-microbial agents as glycerol monolaurate at substantial concentrations while maintaining its anti-microbial effectiveness. Calvert et al. address that long-standing problem by providing formulations of highly soluble, stable liquid crystal mixture of biologically active fatty acid esters (salts and/or glycerol(s)) in an anhydrous polyhydric alcohol system in which the antimicrobial action of the fatty acid esters is maintained.

Monoglycerides are generally recognized as safe (GRAS) benign, non-toxic substances that are often used as emulsifiers for food and cosmetic products. Certain monoglycerides have been known to have powerful antimicrobial properties. Breast milk contains high amount of glycerides and it is suggested that infants employ these glycerides to protect against pathogens until their immune systems are fully functioning, some months after birth. Infant formulas typically contain coconut oil or other forms of lauric acid to provide similar protection. It has been well-documented that a paradox exists with regards to *C. difficile* that infants up to one year old have a much higher rate of asymptomatic carriage of *C. difficile* than all other populations, however they rarely develop *C. difficile* infections. Up to 50% of infants typically have detectable *C. difficile* as compared to approximately 3% of adults, but it is rare for infants to express colitis due to *C. difficile*.

Polyglycerol and monolaurin are effective at inhibiting the growth of multiple genera of bacteria and parasites that reside in the intestines of a mammal which have the capacity of cause infection presented as diarrhea or colitis. Those species inhibited by polyglycerol and monolaurin include, but are not limited to *C. difficile, Salmonella typhosa, Salmonella paratyphi, Salmonella schottmuelleri, Shigella dysenteriae, Shigella flexneri, Proteus vulgaris, Pseudomonas aeruginosa, Listeria,* and *Escherichia coli.* In addition, *Bacteroides* species such as *B. fragilis, B. uniformis,* are also inhibited by polyglycerol and monolaurin.

The results of in vitro studies show that the stable liquid crystal mixture of biologically active fatty acid esters inhibits the growth of *C. difficile* at concentrations consistent with nutritional supplements.

There is thus a long-standing need in the medical community for highly effective compositions and methods for the treatment of bacterial infections, including those by *C. difficile*. By combining a highly soluble, stable liquid crystal mixture of biologically active, medium-chain fatty acid esters in a polyhydric alcohol solvent with broad-range antimicrobial efficacy with probiotic treatment, the present invention addresses that need.

SUMMARY OF THE INVENTION

The present invention relates to the administration of a novel liquid crystal mixture comprised of medium chain monoglycerides and biologically active fatty acid esters that inhibit the growth of pathogenic bacteria in the intestines of a mammal. Said liquid crystal mixture may be administered in conjunction with a probiotic blend at various intervals over the treatment period to effectively inhibit pathogenic bacterial growth and increase the flora of healthy bacteria, thereby controlling and curing various pathogenic enteric infections.

In certain embodiments, the overall therapy includes two steps: 1) a conventional probiotic supplement or food that consists of colony forming units (CFU's) of beneficial microorganisms; and 2) a separate dose of a soluble, digestible liquid crystal mixture of medium chain monoglycerides, which in certain preferred embodiments is glycerol monolaurate. The objective of the therapy is to promote the growth of beneficial intestinal flora by conventional seeding of beneficial organisms and, uniquely, by directly inhibiting the growth of potentially pathogenic bacteria such as C. difficile using a powerful, but benign, non-toxic antimicrobial agent.

The present invention, therefore, includes a powerful and unique tool for promoting a population of intestinal flora by both significantly inhibiting the proliferation of harmful bacteria and not significantly inhibiting the growth of beneficial probiotic symbionts through the co-administration of polyglycerol monolaurin and a probiotic dietary supplements.

In addition to fatty acid monoesters and probiotics, other additives, ingredients, or compounds may be added to the present invention to further functionalize the therapy.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 1 displays the results of minimum inhibitory concentration test of two liquid crystal mixtures against C. difficile.;

FIG. 2 shows the results of minimum inhibitory concentration test of a third liquid crystal mixture against C. difficile.; and FIG. 3 displays the results of a minimum inhibitory concentration test of a liquid crystal mixture against probiotic microorganisms.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided herein below with reference to the attached drawings.

The present invention provides a stable liquid crystal mixture of biologically active fatty acid esters in a base of polyglycerol with antimicrobial efficacy. The present invention further provides a liquid crystal mixture of biologically active fatty acid esters in a base of polyglycerol composition with increased solubility in the magnitude of 20-30 times over existing polyglycerol monolaurin compositions. The present invention includes liquid crystal mixtures of biologically active fatty acid esters in a base of polyglycerol composition having decreased incidence of problematic crystallization upon formulation in various pharmaceutical vehicles. The liquid crystal mixtures may also include a polyhydric alcohol as a solubilizer. The liquid crystal mixtures of biologically active fatty acid esters in a base of polyglycerol compositions of the present invention may be taken internally by a patient to control and stop infections of the intestines caused by pathological enteric bacteria. The present invention may also include the liquid crystal mixtures of biologically active fatty acid esters taken in conjunction with an antibiotic regimen.

Within this application, "liquid crystal mixture" means a liquid crystal mixture formed by the preferred embodiment wherein at least one polyhydric alcohol is combined with at least one medium chain glycerol ester and at least one alkali reactant. The crystals are dynamic and the morphology thereof is determined by concentration of fatty acid ester, type of polyhydric alcohol used, and the temperature of the mixture.

The liquid crystal compositions employed within the present invention may be made in the following manner. A fatty acid ester is introduced into a polyhydric alcohol solvent and heated to a temperature above the melting point of the ester but below the condensation point of the solvent. A predetermined amount of reactant is added to this heated mixture resulting in the partial hydrolysis, also known as saponification, of the ester constituent and subsequently forms the ester salt thereof. Mixing these components results in a stable liquid crystalline mixture wherein the ester and ester salt are within a polyhydric alcohol solvent. In certain preferred embodiments, no water is added in the process.

Examples of fatty acid esters are glyceryl or glycerol monesters (monoglycerides) with carbon chain lengths of between $C_6$-$C_{32}$ including, but not limited to, glycerol monocaprylin, glycerol monocaprin, glycerol monolaurin, glycerol monostearate, etc. and mixtures thereof. Fatty acids employed in the present invention may be a saturated fatty acid having a carbon chain having between 4 and 28 carbon atoms. Examples of fatty acids useful within the context of the present invention include, but are not limited to butyric, isobutyric, succinic, caproic, adipic, caprylic, capric, lauric, myristic, palmitic, and stearic acids, and their monoglycerides and mono-, di- and triglycerides of fatty acids, fatty acid esters of carboxylic acids of at least 6 carbon atoms. Examples of presently preferred monoglycerides include 2,3-dihydroxypropyl decanoate, 2,3-dihydroxypropyl dodecanoate (glycerol monolaurate), 2,3-dihydroxypropyl tetradecanoate (glycerol monomyristate), and 2,3-dihydroxypropyl hexadecanoate (glycerol monopalmitate).

The fatty acid ester is preferably included in the liquid crystal mixture at a concentration from about 10% to about 80%, by weight, of the liquid crystal mixture. The presently preferred concentration of fatty acid ester is between about 20% and about 60%, by weight of the liquid crystal mixture.

Examples of polyhydric alcohols include, but are not limited to, glycerin, diglycerine, glycerol, diglycerol, triglycerol, tetraglycerol and polyglycerols having a higher degree of condensation, 1,3-butylene glycol, propylene glycol, dipropylene glycol, triethylene glycol, polyoxypropylene glyceryl ether, polyoxypropylene diglyceryl ether, neopentyl glycol, trimethylolethane, trimethylolpropane, polyoxypropylene, glycol, trimethylolethane, trimethylolpropane, tetraglycerol, pentaglycerol, hexaglycerol, heptaglycerol, and polyglycerols having a carbon chain length of greater than seven.

Examples of strong basic agents are alkali and alkaline-earth metal hydroxides, such as lithium, sodium, potassium, and calcium hydroxides; alkali and alkaline-earth metal alkoxides, such as sodium, potassium and magnesium methoxides, ethoxides, isopropoxides and tert-butoxides, and aluminium isopropoxide, preferably sodium hydroxide, potassium hydroxide, and sodium methoxide, with a particularly preferred example being potassium hydroxide.

The polyhydric alcohol is preferably included in the liquid crystal mixture at a concentration that is approximately 20% to approximately 90%, by weight. The level of polyhydric alcohol is largely complementary to that of the ester, excluding side products of the reaction. For example, a liquid crystal mixture containing 40% fatty acid ester would include 60% polyhydric alcohol. A particularly preferred liquid crystal mixture contains 60% glycerol monolaurin as the fatty acid ester and 40% polyglycerol. An example is provided in the table following.

| Starting Reactants | | Calculated estimate of final LCM | |
|---|---|---|---|
| KOH (55% aq) | 2.91% | Glycerol monolaurate | 48-52% |
| Polyglycerol | 38.83% | Polyglycerol | 38-40% |
| Glycerol monolaurin | 58.25% | Potassium laurate | 3-6% |
| | | Glycerol | 1-3% |
| | | Water | <1.5% |

As is seen from the table above, the final composition also includes a small percentage of the potassium salt of the monoglyceride.

In certain presently preferred embodiments, the liquid crystal compositions may be taken by patients in conjunction with a probiotic dietary supplement in order to cleanse and eliminate the intestines of pathogenic bacteria while at the same time reintroducing healthy probiotic colony forming units in order to fortify the intestinal health of a patient. The present invention further provides a daily intestinal health regime wherein a liquid crystal mixture of biologically active fatty acid esters in a base of polyglycerol composition is taken at between approximately 2 and approximately 6 hours apart from a probiotic dietary. In some embodiments of the present invention, a probiotic dietary supplement that contains toxin binding agents may be employed with the liquid crystal compositions. The liquid crystal compositions of the present invention may be taken by patients orally, rectally, or parenterally. The compositions of the present invention preferably prevent the recurrence of intestinal infection. These and other objects of the present invention will become readily apparent upon further review of the following detailed description.

A preferred method of providing a liquid crystal mixture of polyglycerol oligomers and biologically active medium chain glycerol fatty acid esters (LCM) composition with enhanced solubility and stability wherein said composition is able to be added to a topical formulation at weight percents from 1 to greater than up 60% (wt/wt %) without significant crystallization or separation in order to provide a resultant material that possesses broad range antimicrobial properties is disclosed in U.S. Patent Application No. 61/252,269 by Calvert et al.

The LCM composition of the present invention is effective at inhibiting the growth of certain pathologic enteric bacteria in patients, while not significantly affecting the growth or life cycle of common, healthy enteric bacteria. A combination of the LCM composition with antibiotics, probiotics, and other ingredients provides for a novel new treatment for intestinal infections and may prevent subsequent infections if taken as a maintenance product.

As used throughout this application, the term "patient" refers to mammals, including humans. The present invention is particularly useful in treating patients having a *C. difficile* infection or to promote healthy intestinal bacterial flora.

The compositions of the present invention may be included in a diversity of pharmaceutically acceptable formulations. Those formulations may include additional components to render the composition appropriate for administration to patients. The compositions of the present invention may be formulated as a capsule, soft gel, atomizable liquid, or suppository. In other embodiments, the compositions of the present invention may be included in a functional food product including, but not limited to baked goods, dairy products, non-dairy products, functional beverages, confections, or candies.

For therapeutic use in the method of the present invention, the LCM may be conveniently administered in the form of a pharmaceutical composition containing one or more pharmaceutically acceptable carriers, Suitable carriers are well known in the art and vary with the desired form and mode of administration of the pharmaceutical composition. For example, they may include diluents or excipients such as fillers, binders, wetting agents, disintegrators, surface-active agents, glidants, lubricants, and the like. Typically, the carrier may be a solid, liquid, or vaporizable carrier, or combinations thereof. Each carrier is preferably "acceptable" in the sense of being compatible with the other ingredients in the composition and not injurious to the patient. The carrier is preferably biologically acceptable and inert, i.e., it permits the LCM compound(s) to inhibit the development of the pathogen and, particularly, the toxins evolved thereof.

Suppositories are bodies of solid materials into which medications have been incorporated. These medications are then placed into body cavities. Medications are released at the site of placement, resulting in local effects of the medications.

Suppository forms of medications are available for placement in the anus and vagina for the treatment of anorectal and gynecologic disorders. The most common use of rectal suppositories is for the treatment of constipation. Rectal suppositories are also used as an alternative form of drug delivery in patients that cannot receive medications by mouth. Examples of these types of rectal suppositories include treatments for nausea and pain.

The LCM of the present invention may be administered directly into the rectum via suppository, enema, or colonic rinse would deliver the LCM directly to the infection site. In addition, many *C. difficile* infections lead to pseudomembranous colitis, severe bowel inflammation, toxic megacolon, and potentially a blockage leading to sespsicemia and potential death. In the case wherein there is blockage in the intestinal tract, the administration of a rectal suppository could facilitate treatment.

Suppositories may be constructed from fatty (or oleaginous) bases and/or water-soluble (or miscible) bases. Fatty bases include theobroma oil (also known as cocoa butter) with or without spermacetic or beeswax to raise the suppository melting point. Additionally, fatty bases for the LCM suppositories may include synthetic triglycerides and hydrogenated vegetable oils. These may include palm, palm kernel or coconut oils. Name brands utilized for production of vitamin. The following fatty bases may also be used in the formulation of suppositories of the present invention.

| TRADE/COMMON NAME | INGREDIENTS | MANUFACTURER/SUPPLIER |
|---|---|---|
| PCCA Base MBK ™ | Fatty Acid Base | PCCA* |
| PCCA Base A ™ | Polyglycol 1450 MW, NF | PCCA* |
| PCCA Base F ™ | Synthetic Cocoa Butter | PCCA* |
| Wecobee ® M, R, S, W | Vegetable oil, hydrogenated | Stephan Company, Northfield, IL |
| Witepsol ® H12, H15, W35 | Vegetable oil, hydrogenated | Stephan Company, Northfield, IL |
| Hydrokote ® M | Vegetable oil, hydrogenated | Abitec Corporation, Columbus, OH |
| COA Base | Fatty Acid Base | Spectrum Pharmacy Products, Tuscon, AZ |
| Supposibase | PEG/Vegetable Oil | Spectrum Pharmacy Products, Tuscon, AZ |
| Base A, B, D | Polyethylene Glycols | Spectrum Pharmacy Products, Tuscon, AZ |
| Polybase | Polyethylene Glycol Blend | Gallipot, Inc., St Paul, MN |

*Professional Compounding Centers of America, Inc., Houston TX

Water-soluble bases may include glycerated gelatin, with or without preservatives, and polyethylene glycol polymers. Suppositories may be constructed by hand rolling, compression molding or fusion molding methods.

Administration of the LCM as a suppository has such advantages as: 1) Larger doses may be delivered directly to the afflicted area, resulting in more potent and effective therapy for the patient. 2) The amount of the delivered LCM will undergo much less or no absorption into the systemic circulation. For certain substances, particularly the LCM of the present invention, no toxic effects of the compound will be seen.

Typical formulations of LCM suppositories would include 100-1000 mg LCM in an appropriate suppository base.

For example, a typical total suppository may weigh 700-1200 mg. An example formulation is 500 mg LCM with 250 mg MBK/Wax. The LCM of the formulation may be composed of approximately 55% glycerol monolaurate, 38% polyglycerol, 5% potassium laurate, 1% glycerin, and <1% moisture.

The LCM may be mixed with a carrier to adjust for viscosity and to enable processing including, but not limited to coconut oil, almond oil, olive oil, palm kernel oil, peanut oil, sunflower oil, corn oil, sesame oil, palm oil, safflower oil, soybean oil, cottonseed oil, rapeseed oil, a modified synthetic oil, or mixtures thereof. A particularly preferred carrier oil is coconut oil. The present invention preferably utilizes about 0.5-80% carrier oil, more preferably about 15-40%, most preferably about 27.5%.

In addition, emulsifiers may be used to keep the oil and LCM combined during processing and packaging. Such emulsifiers include but are not limited to lecithin, mono- and diglycerides, propylene glycol monoesters, lactylated esters, polyglycerol esters, sorbitan esters, ethoxylated esters, succinylated esters, fruit acid esters, acetylated monoglycerides, phosphated esters, sucrose esters, or mixtures thereof. The emulsifier component may comprise a single emulsifier or a combination of emulsifiers. A particularly preferred emulsifier is lecithin. The present invention preferably utilizes about 0.5-10% emulsifier, more preferably about 1-5%, most preferably approximately about 2.5%.

The present invention further includes the administration of LCM to patients that selectively kills certain Gram-positive and Gram-negative pathogenic bacteria used in combination with health-promoting probiotic organisms functions to militate against the deleterious physiological effects of the antibiotic therapy and reverse pathological bacterial infections of the intestines.

The LCM/probiotic regimen of the present invention may be administered to patients to prevent recurrent *C. difficile* infection as well as treat active infection. The LCM is preferably administered at least 4 hours apart from the probiotic supplement to allow for the probiotic species to enter the gut and become established. For inhibition of pathogenic bacteria, the present invention preferably administers a therapeutically effective amount of LCM in a dosage of about 50 mg to about 2500 mg per day and the probiotic supplement is administered in a dosage of about 0.5 to about 5 grams of a 1 million to 30 billion CFU/g probiotic containing at least one of *Lactobacillus brevis, Lactobacillus bulgaricus, Lactobacillus plantarum, Lactobacillus rhamnosus, Lactobacillus fermentum, Lactobacillus caucasicus, Lactobacillus helveticus, Lactobacillus lactis, Lactobacillus reuteri, Lactobacillus casei, Bifidobacterium bifidum, Bifidobacterium longum, Bifidobacterium infantis*, and *Bifidobacterium lactis*. More preferably the LCM is administered in a dosage of about 100 to about 1000 mg and the probiotic supplement is administered in a dosage of about 100 to about 1000 mg of a potency of 10 billion CFU/g. Most preferably, the LCM is administered in a dosage of about 350 to about 500 mg per day and the probiotic is administered in a dosage of 1000 grams of a potency of 10 billion CFU/g In one embodiment of the present invention, from about 100 to about 4000 mg of the LCM composition is provided in two part capsules and is taken by a patient for 30-365 days over the course of a year. In addition, from 100 to 3000 mg of a 30 billion CFU/gram blend of *Lactobacillus brevis, Lactobacillus bulgaricus, Lactobacillus plantarum, Lactobacillus rhamnosus, Lactobacillus fermentum, Lactobacillus caucasicus, Lactobacillus helveticus, Lactobacillus lactis, Lactobacillus reuteri, Lactobacillus casei, Bifidobacterium bifidum, Bifidobacterium longum, Bifidobacterium infantis*, and *Bifidobacterium lactis* is taken 12 hours apart from the administration of the LCM.

In another embodiment, about 100 to about 4000 mg of the LCM composition is provided as encapsulated in soft gelatin (soft gels) and is taken by a patient for 30-365 days over the course of a year.

In addition, from about 100 to about 3000 mg of a 30 billion CFU/g blend of *Lactobacillus brevis, Lactobacillus bulgaricus, Lactobacillus plantarum, Lactobacillus rhamnosus, Lactobacillus fermentum, Lactobacillus caucasicus, Lactobacillus helveticus, Lactobacillus lactis, Lactobacillus reuteri, Lactobacillus casei, Bifidobacterium bifidum, Bifido-

*bacterium longum, Bifidobacterium infantis*, and *Bifidobacterium lactis* is taken 12 hours apart from the administration of the LCM.

In another embodiment, about 50 to about 4000 mg of the LCM composition is administered in conjunction with a probiotic supplement that contains *Saccaromyces boulardii*.

In another embodiment, about 50 to about 4000 mg of the LCM composition is administered in conjunction with an antibiotic treatment in order to control *Clostridium* infection. Said LCM composition may be administered during antibiotic treatment and for a duration of about 5 to about 120 days following said antibiotic treatment.

In another embodiment, the LCM composition of the present invention is administered to a patient undergoing a course of therapy for the treatment of *C. difficile* colitis by antibiotic including but not limited to bacitracin, cefprozil, meropenem, metronidazole, nitazoxanide, ricarcillin; clavulanic acid, tinidazole, vancomycin or other components with the objective of assisting treatment and preventing a recurrence. Said patient is administered about 50 to about 4000 mg of the LCM composition in capsule, soft gel, or suppository during antibiotic treatment and from about 5 to about 120 days following antibiotic treatment.

In another embodiment, about 50 to about 4000 mg of the LCM composition is supplied encapsulated in soft gel, capsules, injectable, or as a suppository and delivered to health care professionals upon observation of *C. difficile* outbreak in or around an institutional setting including, but not limited to hospitals, nursing home, clinic, kennel, barn, or stables.

In another embodiment, about 10 to about 2000 mg of the LCM composition is supplied as a soft gel, capsule, sterile injectable, or rectal suppository is supplied in combination with a probiotic supplement in order to maintain healthy intestinal function and reduce the risk of pathogenic intestinal infection as caused by bacteria, protozoa, ameba, fungi, virus, or other pathogen including but not limited to *C. difficile, Salmonella typhosa, Salmonella paratyphi, Salmonella schottmuelleri, Shigella dysenteriae, Shigella flexneri, Proteus vulgaris, Pseudomonas aeruginosa, Listeria* and *Escherichia coli, B. fragilis*, or *B. uniformis, Candida albicans*, and enveloped viruses.

In yet another embodiment, the LCM composition is provided in a functional food including, but not limited to baked goods, dairy products, non-dairy products, functional beverages, confections, candies, or other wherein said LCM composition is provided from about 50 to about 4000 mg per day.

In yet another embodiment, the LCM composition is provided in a functional food or function beverage also contains probiotic colony forming units wherein said LCM composition is provided from about 50 to about 4000 mg per serving and wherein said probiotics are provided from 5 to 50 billion CFUs/g per serving.

In yet another embodiment, about 50 to about 4000 mg of the LCM composition in the form of a soft gel, capsule, functional food, functional beverage, or suppository is provided with from 5 to 50 billion CFU of probiotics and a dietary supplement containing 50-1000 mg calcium disodium EDTA, 100-500 mg psyllium powder, and 10-50 mg delta tocotrienols in order to assist in addressing Gram-negative enteric bacteria and to reduced, bind, and eliminate common toxins resulting from over growth of pathologic enteric bacteria.

In another embodiment, about 50 to about 4000 mg of the LCM composition is provided with about 20 to about 1000 mg of fish oil and about 0.1 to about 100 mg oragnium oil as a dietary supplement. Said supplement is administered with from 5 to 50 billion CFU of probiotics and a dietary supplement containing 50-1000 mg calcium disodium EDTA, 100-500 mg psyllium powder, and 10-50 mg delta tocotrienols in order to assist in addressing gram negative enteric bacteria and to reduced, bind, and eliminate common toxins resulting from over growth of pathologic enteric bacteria.

In another embodiment, about 50 to about 4000 mg of the LCM composition in the form of a soft gel, capsule, functional food, functional beverage, or suppository and is administered along with extracts of oraginum and a multivitamin.

Many whole botanical extracts possess antimicrobial efficacy due to composition. Examples of active compounds in botanicals include, but are not limited to terpenes (e.g., beta.-phellandrene, with beta-bisabolene, beta-caryophyllene, beta-phellandrene, alpha- and beta-pinene, limonene, linalool, borneol, acetaldehyde, menthadienes, and nitromenthadienes, p-cymene, γ-terpinene), triterpenes, lactones (e.g., tridecanolide, 12-methyl tridecanolide, pentadecanolide), alkaloids (e.g., xanthopuccine, berberine, hidrastine, hidrastanine, beta-hydrastine, canadine and canadaline), glucans, sterols (e.g., beta-sitosterol, campesterol, stigmasterol), polyphenols (e.g., thymol, carvacrol, flavanols, oligomeric proanthocyanidins (OPC), glycosides (e.g., echinacoside), amides (e.g., echinacein, isobutylamides), terpenoids (e.g., germacrane), polysaccharides, phenolic acids (e.g., chlorogenic and hydroxycinnamic, gallic acids), organic acids (e.g., gallic, caffeic, and chlorogenic acids), saponins, GABA (gamma aminobutyric acid), benzenoids and flavonoids (e.g., beta-lapachone, xyloidone, tabebuin, quercetin, tecomine, steroidal saponins), hirsutine, tannins, catechins, oligomeric procyanadins (e.g., 1-epicatechol), cyanogenetic glycosides, diterpenoids (e.g., hardwickiic acid, bincatriol, crolechinol, crolechinic acid, coberine A, coberine B), fatty acids, and resin.

Other potential additives to the present invention include vitamins/antioxidants (ascorbic acid, B vitamins, tocopherols, tocotrienols, carotene, menaquinone, phyloquinone, calciferol, calcitriol, etc.), extracts (resveratrol, astragulous, hawthorne berry, etc.) surfactants, amino acids (taurine, L-carnitine, arginine, ornithine, lysine), chelating agents (calcium disodium EDTA, meso-2,3-dimercaptosuccinic acid (DMSA), etc.), pharmaceuticals (antibiotics, antifungals, etc.), excipients (carrier oils, fillers, lubricants, free flow agents, binders, gelatin), or other compounds.

In addition to fatty acid monoesters and probiotics, other additives, ingredients, or compounds may be added to the present invention to further functionalize the therapy. Certain natural oils and plant essences have shown to be effective in killing and inhibiting growth of pathogens such as bacteria, *Bacteroides*, viruses, amoebas, protozoans, yeasts, fungi, cestoids, annalids, flukes, and other microorganisms. Botanical extracts, tinctures, oils, and waters with desired antimicrobial efficacy include, but are not limited to thyme oil, ajowan oil, citronella oil, olive oil, cinnamon oil, geranium oil, eucalyptol oil, peppermint oil, mint oil, thymol, eugenol, verbenone, eucalyptol, terpineol, cinnamic acid, methyl salicylic acid, limonene, geraniol, and oraginum oil.

Thus, in accordance with the invention, fatty acid monoesters, preferably glycerol monolaurate, delivered as a stable liquid crystal mixture of biologically active fatty acid esters in a base of polyglycerol, namely tri- and di-glycerol, compounds co-administered with a probiotic supplements can address, arrest, and cure infections of the intestines of mammals. To demonstrate the biocidal effectiveness of the present invention, the following experiments were carried out.

FIG. 1 shows the results of minimum inhibitory concentration (MIC) test for two LCMs, PC-06 and PC-07 against *C.*

*difficile*. PC-06, composed of approximately 80% glycerol monoester, showed complete inhibition at 0.016%, while PC-07, composed of approximately 60% glycerol monoester, showed complete inhibition at 0.004%. The difference in inhibition is attributable to the more viscous nature of PC-06, however both formulations display inhibition at therapeutically relevant concentrations.

FIG. 2 shows the MIC data for a liquid crystal mixture when tested against *C. difficile*. BPS-K-360 is a presently preferred formulation used in the present invention and is composed of approximately 74% liquid crystal mixture, 23.5% refined coconut oil, and 2.5% lecithin. The liquid crystal mixture contained approximately 45-60% by weight glycerol monoester. The mixture showed complete inhibition of *C. difficile* at 0.008% dilution.

FIG. 3 shows the minimum inhibitory concentration data of the same LCM of BPS-K-360 against common probiotic bacteria and the beneficial yeast *S. boulardii*. As the data show, the MIC values for inhibition of these beneficial microorganisms are near those of the MIC for *C. difficile* disclosed in FIGS. 1 and 2 above. Such results implicate the utility of co-administering a probiotic supplement with the liquid crystal mixtures when treating patients for *C. difficile* infections.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

We claim:

1. A method of treating intestinal infections comprising the steps of:
administering to a patient in need thereof a composition comprising a liquid crystal mixture of antimicrobial glycerol fatty acid esters and a polyhydric alcohol; and
administering to said patient a probiotic dietary supplement.

2. The method of claim 1, wherein said liquid crystal mixture contains at least one fatty acid ester selected from the group consisting of one mono-, di-, and triglyceride of a saturated fatty acid having a carbon chain with a number of carbon atoms numbering between 4 and 28 carbon atoms.

3. The method of claim 1, wherein said at least one monoglyceride is selected from the group consisting of 2,3-dihydroxypropyl decanoate, glycerol monolaurate, glycerol monomyristate, and glycerol monopalmitate.

4. The method of claim 1, wherein said polyhydric alcohol is selected from the group consisting of glycerin, diglycerine, 1,3-butylene glycol, propylene glycol, polypropylene glycol, polyoxypropylene glyceryl ether, polyoxypropylene diglyceryl ether, neopentyl glycol, trimethylolethane, trimethylolpropane, glycerol, diglycerol, triglycerol, propylene glycol, dipropylene glycol, tripropylene glycol, tetraglycerol, pentaglycerol, hexaglycerol, heptaglycerol, and polyglycerols having a carbon chain length of greater than seven.

5. The method of claim 1, wherein said liquid crystal mixture is delivered at an amount between approximately 5 and 4000 mg per day.

6. The method of claim 1, wherein said probiotic dietary supplement contains therapeutically effective amount of at least one supplement selected from the group consisting of *Lactobacillus brevis, Lactobacillus bulgaricus, Lactobacillus plantarum, Lactobacillus rhamnosus, Lactobacillus fermentum, Lactobacillus caucasicus, Lactobacillus helveticus, Lactobacillus lactis, Lactobacillus reuteri, Lactobacillus casei, Bifidobacterium bifidum, Bifidobacterium longum, Bifidobacterium infantis, Bifidobacterium lactis*, and *Saccharomyces boulardii*.

7. The method of claim 1, wherein said probiotic supplement is delivered at an amount between approximately 100 and 3000 mg per day.

8. The method of claim 7, wherein said probiotic dietary supplement includes approximately 5-30 billion CFU/g of probiotic organisms.

9. The method of claim 1, wherein said liquid crystal mixture is provided as a capsule, soft gel, or rectal suppository.

10. A method of treating *C. difficile* intestinal infections comprising the steps of:
administering to a patient in need thereof a composition comprising a liquid crystal mixture, an emulsifier, and a carrier oil, wherein said liquid crystal mixture comprises at least one antimicrobial glycerol fatty acid ester at a concentration of about 10% to 80%, by weight of said liquid crystal mixture, and a polyhydric alcohol at a concentration of about 20% to 90%, by weight of said liquid crystal mixture; and
administering to said patient in need thereof a probiotic dietary supplement.

11. The method of claim 10, wherein said biologically active glycerol fatty acid ester is selected from the group consisting of monoglycerides having carbon chain lengths of between $C_6$-$C_{32}$.

12. The method of claim 10, wherein said biologically active glycerol fatty acid ester is selected from the group consisting of 2,3-dihydroxypropyl decanoate, glycerol monolaurate, glycerol monomyristate, and glycerol monopalmitate.

13. The method of claim 10, wherein said liquid crystal mixture is administered at an amount between approximately 5 and 4000 mg per day.

14. The method of claim 10, wherein said composition includes between approximately 0.5% and 90%, by weight, of said carrier oil.

15. The method of claim 14, wherein said carrier oil is coconut oil, almond oil, olive oil, palm kernel oil, peanut oil, sunflower oil, corn oil, sesame oil, palm oil, safflower oil, soybean oil, cottonseed oil, rapeseed oil, a modified synthetic oil, or mixtures thereof.

16. The method of claim 10, wherein said composition includes between approximately 0.5% and 10%, by weight, of said emulsifier.

17. The method of claim 16, wherein said emulsifier is lecithin, mono- and diglycerides, propylene glycol monoesters, lactylated esters, polyglycerol esters, sorbitan esters, ethoxylated esters, succinylated esters, fruit acid esters, acetylated monoglycerides, phosphated esters, sucrose esters, or mixtures thereof.

18. The method of claim 10, wherein said probiotic dietary supplement contains therapeutically effective amount of at least one supplement selected from the group consisting of *Lactobacillus brevis, Lactobacillus bulgaricus, Lactobacillus plantarum, Lactobacillus rhamnosus, Lactobacillus fer-* mentum, *Lactobacillus caucasicus*, *Lactobacillus helveticus*, *Lactobacillus lactis*, *Lactobacillus reuteri*, *Lactobacillus casei*, *Bifidobacterium bifidum*, *Bifidobacterium longum*, *Bifidobacterium infantis*, *Bifidobacterium lactis*, and *Saccharomyces boulardii*.

19. The method of claim 18, wherein said probiotic supplement is delivered at an amount between approximately 100 and 3000 mg per day.

20. The method of claim 19, wherein said probiotic dietary supplement includes approximately 5-30 billion CFU/g of probiotic organisms.

21. The method of claim 10, wherein the administering of said liquid crystal mixture to said patient occurs between about two and about six hours apart from the administration of said probiotic supplement.

22. The method of claim 10, wherein said administering steps are performed repeatedly for 30 to 365 days.

23. The method of claim 10, wherein said polyhydric alcohol is selected from the group consisting of glycerin, diglycerine, 1,3-butylene glycol, propylene glycol, polypropylene glycol, polyoxypropylene glyceryl ether, polyoxypropylene diglyceryl ether, neopentyl glycol, trimethylolethane, trimethylolpropane, glycerol, diglycerol, triglycerol, propylene glycol, dipropylene glycol, tripropylene glycol, tetraglycerol, pentaglycerol, hexaglycerol, heptaglycerol, and polyglycerols having a carbon chain length of greater than seven.

24. A method of treating *C. difficile* intestinal infections in a patient comprising the steps of:
    administering to said patient in need thereof a composition comprising by weight 74% of a liquid crystal mixture, 2.5% of lecithin, and 23.5% coconut oil, wherein said liquid crystal mixture comprises approximately 40% to 60%, by weight of the liquid crystal mixture, of glycerol monolaurate and approximately 40% to 60%, by weight of the liquid crystal mixture, a polyhydric alcohol; and
    administering to said patient in need thereof a probiotic dietary supplement that contains at least one supplement from the group consisting of *Lactobacillus brevis*, *Lactobacillus bulgaricus*, *Lactobacillus plantarum*, *Lactobacillus rhamnosus*, *Lactobacillus fermentum*, *Lactobacillus caucasicus*, *Lactobacillus helveticus*, *Lactobacillus lactis*, *Lactobacillus reuteri*, *Lactobacillus casei*, *Bifidobacterium bifidum*, *Bifidobacterium longum*, *Bifidobacterium infantis*, *Bifidobacterium lactis*, and *Saccharomyces boulardii*.

\* \* \* \* \*